United States Patent [19]

Hudak et al.

[11] Patent Number: 5,641,637

[45] Date of Patent: Jun. 24, 1997

[54] METHOD OF PREPARING LYOPHILIZED AND FROZEN CELL STANDARDS

[75] Inventors: Robert Hudak, Landenberg, Pa.; Iris Williams, Compton, Calif.; Vijay Adda, South Pasadena, Calif.; Raymond P. Goodrich, Jr., Pasadena, Calif.

[73] Assignee: Cobe Laboratories, Inc., Lakewood, Colo.

[21] Appl. No.: 43,394

[22] Filed: Apr. 5, 1993

Related U.S. Application Data

[63] Continuation-in-part of Ser. No. 786,109, Nov. 1, 1991, abandoned, which is a continuation-in-part of Ser. No. 695,169, May 3, 1991, abandoned, which is a continuation-in-part of Ser. No. 639,937, Jan. 11, 1991, abandoned.

[51] Int. Cl.$^6$ ............................................. G01N 33/96
[52] U.S. Cl. .................. 435/7.24; 435/2; 435/260; 436/8; 436/10; 436/18; 436/176; 436/826; 424/529; 424/534
[58] Field of Search .......................... 435/7.24, 2, 29, 435/240.2, 243, 260; 436/8, 18, 10, 172, 176, 805, 826; 424/529, 535

[56] References Cited

U.S. PATENT DOCUMENTS

| | | |
|---|---|---|
| 4,865,871 | 9/1989 | Livesey et al. . |
| 5,059,518 | 10/1991 | Kortright .................. 435/6 |
| 5,178,884 | 1/1993 | Goodrich .................. 424/533 |
| 5,242,792 | 9/1993 | Rudolph et al. . |

FOREIGN PATENT DOCUMENTS

| | | |
|---|---|---|
| 44118/89 | 5/1990 | Australia . |
| 46166/89 | 6/1990 | Australia . |
| 77248/91 | 2/1992 | Australia . |
| 0469766 | 2/1992 | European Pat. Off. . |
| 475409A2 | 3/1992 | European Pat. Off. . |
| WO87/05300 | 9/1987 | WIPO . |
| 42837 | 10/1989 | WIPO . |
| 44118 | 10/1989 | WIPO . |
| WO90/09432 | 8/1990 | WIPO . |

OTHER PUBLICATIONS

Prince, H.E. et al, Journal of Immunological Methods vol. 93 pp. 15–18 1986.

*Primary Examiner*—Paula K. Hutzell
*Assistant Examiner*—Rachel Heather Freed
*Attorney, Agent, or Firm*—Finnegan, Henderson, Farabow, Garrett & Dunner, L.L.P.

[57] ABSTRACT

A method is disclosed for preparing lyophilized and frozen cells as cytometry standards.

13 Claims, No Drawings

METHOD OF PREPARING LYOPHILIZED AND FROZEN CELL STANDARDS

This application is a continuation-in-part of commonly assigned Ser. No. 07/786,109, filed Nov. 1, 1991 (abandoned), which is a continuation-in-part of Ser. No. 07/695,169, filed May 3, 1991 (abandoned), which in turn is a continuation-in-part of Ser. No. 07/639,937, filed Jan. 11, 1991 (abandoned), the disclosures of which are all incorporated by reference herein in their entirety.

The present invention is directed to freeze-dried cell standards and methods for preparation thereof, which are particularly useful as analytical standards which otherwise would require fresh (i.e., not previously frozen or lyophilized) cells. The cells are particularly useful as standards for flow cytometry. The invention is particularly directed to standards comprising lymphocytes and granulocytes which are freeze-dried and then reconstituted as standards which preserve light scattering characteristics and the ability to be stained for CD4:CD8 fluorescent assays.

BACKGROUND OF THE INVENTION

There are several analytical methods for measuring characteristics of cells and cell-like materials (such as liposomes) which require the use of fresh, live cells for standardization of the equipment. The most important of these methods is flow cytometry, the measurement of cells in a moving liquid stream, which is a valuable analysis tool in research laboratories. In the apparatus used in cytometry, called a cytometer or flow cytometer, a fluid flows through a sensing orifice in the presence of an electric field. If the particle enters the orifice it will disturb the electric field, increasing the resistance of the circuit and the size of the disturbance will be proportional to the volume and relative particle size to the volume of the orifice. An electric pulse is caused as each particle passes through the orifice, and the pulse height will be proportional to the size of the particle. Using sophisticated focusing techniques to enhance the resolution, the flow cytometer can be used for electrical sizing of the cells. Furthermore, if the cells are chemically tagged with fluorescent molecules when they are flowed past a source of monochromatic light (a laser), a lens system can be used to detect the amount of light scattered as well as the fluorescent signals. The scattered light intensity is a complex function of cell size and refractive properties of the cell but generally it can be used as a way of measuring the cell area. The fluorescent signals are roughly a measure of the concentration of the fluorescent molecule in a cell or on its surface. The wide angle scatter of the light can be measured as a tool for distinguishing cells of equal size which have different internal refraction properties. For example, cells with more internal structure such as granulocytes, will scatter more light at right angles than will lymphocytes. Therefore, the flow cytometer is an instrument for rapid and accurate measurement of particle volume (electrical resistance sizing), particle area (forward light scatter), fluorescent atom concentration (fluorescent emission), and particle granularity (right angle light scatter). If a charging pulse is applied to the stream, cells can be selectively deflected into distinct streams and the cells in those streams counted. In this way the flow cytometer is also a tool for sorting and counting cells.

The present invention is directed to providing materials for calibrating cell-analyzing apparatus such as a flow cytometer. The accuracy of the flow cytometer is directly related to the ability to calibrate the system with calibrating particles which should be highly stable, readily available particles of known size and light scattering characteristics. One of the calibrating standards typically used is a plastic bead, but in many instances these are unsatisfactory since a solid sphere (which does not deform) displaces additional current at its leading and trailing edge. As a result an electrical sizing system will over estimate the size of a plastic sphere, usually by a factor of about 1.5.

If one is to use the flow cytometer to measure live cells, then it must be calibrated with live cells, since a live cell has a different index of refraction than a dead cell. Plastic beads also lack the cell surface antigens which are often measured in blood particles such as lymphocytes. Fluorescence is also difficult to calibrate, since the calibrating particle can degrade from leaching or bleaching of the dye. Accordingly, when used for identifying cell subpopulations, some subpopulations are identified without the use of cell-specific chemical markers. For example, in blood leukocyte populations containing lymphocytes, monocytes and granulocytes, measurements of light scattered by cells at two different angles (commonly called the forward scatter and orthogonal or wide angle scatter) from an incident laser beam can discriminate the three cell types sufficiently for differential leukocyte counting in clinical hematology. With the added use of cell specific chemical markers, such as fluorescent markers, other characteristics of the individual cell subpopulations may be determined by a gated analysis, such as the CD4:CD8 subpopulation of lymphocytes.

Cell standards include polystyrene particles in ranges of sizes and colors consisting of UV-excited blue fluorescent and green-excited orange fluorescent spheres in addition to green fluorescent spheres.

For standardizing immunofluorescent measurements, fixed animal thymocytes labeled with covalently attached dyes have been used. Chicken and rainbow trout erythrocytes have also been used as standards for DNA content estimations (Vindelov, et al., Cytometry 3:328 (1982)). Glutaraldehyde-fixed chicken erythrocytes have also been used since they fluoresce without staining.

U.S. Pat. No. 5,059,518 to Kortright, et al. discloses the lyophilization of mammalian cells as control cells for immunoassays and other hematological measurements. The cells are lyophilized in a solution of trehalose and are rehydrated for use. Trehalose, a disaccharide, does not permeate the cell membranes during lyophilization.

The invention provides further improvement over the art for storage of cells. Hospitals must keep samples of rare type cell standards on hand (such as AB- and rare genotype standards) which are more expensive and difficult to acquire than commonly available cell standards. These must be replaced within the three to four week effective shelf life if they are not used.

Even during the seven weeks of refrigeration of red blood cells in Alsever's suspensions, key metabolites such as ATP, are depleted and slow cell lysis occurs.

There is therefore a need for providing blood samples which have longer refrigerated (or room temperature) storage lives than the refrigerated Alsever's red cell suspensions.

The present invention provides frozen or freeze-dried (lyophilized) cells, including erythrocytes and lymphocytes, having the advantages of convenient dry storage in a ready-to-use format. These cells, when reconstituted, are useful as standards for cytometry.

It is yet another object of the present invention to provide frozen or freeze-dried lymphocytes, monocytes and granulocytes which, when reconstituted, preserve key light scattering, staining ability, particularly for CD4:CD8 ratios.

It is an object of the present invention to provide cell standards for analytical methods by using lyophilized red blood cells, lymphocytes, monocytes or granulocytes.

It is another object of the present invention to provide instrument calibration and quality control standards for flow cytometry.

The present invention permits dry storage of intact cells which after rehydration retain key characteristics to provide cell standards.

SUMMARY OF THE INVENTION

The present invention is directed to methods for freezing or freeze-drying and reconstituting cells which retain light scattering and staining characteristics suitable for use as analytical standards, particularly for cytometry. A particular advantage provided by the invention is the ability to lyophilize, store and reconstitute lymphocytes, granulocytes and monocytes in a manner which retains characteristics suitable for use as cytometry standards.

DESCRIPTION OF THE INVENTION

To freeze or lyophilize cells for subsequent reconstitution as an analytical standard, the cells are immersed in an essentially aqueous protective medium, preferably containing a carbohydrate, in a mixture with at least one type of polymer, including amphipathic polymers, and freezing the solution. The solution may be dried to yield lyophilized cells. When reconstituted by thawing or rehydration, the cells retain light scattering and staining characteristics which are properties observable by cytometry. This method of freezing or lyophilization allows for conditions which maintain the size and structure of the cell, and integrity of the cell membrane and associated surface antigens, without the use of a chemical fixative. As used herein, "cells" include, but are not limited to, red blood cells, reticulocytes (immature red blood cells), and whole blood (plasma and all of the cellular elements of blood) red blood cells coated with antibodies, such as antihuman IgG or antihuman IgM, platelets, lymphocytes, leukocytes, granulocytes, monocytes and cell-like materials, such as hemosomes and liposomes. Liposomes are artificial "cells" made of phospholipids. Liposomes can be manufactured to contain drugs or biological products (proteins) of interest, such as liposome encapsulated hemoglobin (hemosomes), and then frozen or lyophilized and reconstituted according to the present invention. Other cells which are encompassed by the scope of the present invention include hematopoietic stem cells, cancer or hybridoma cultured cell lines, tumor cell explants, or other cultured human or non-human mammalian cells.

The carbohydrate may be selected from the group consisting of monosaccharides, since disaccharides do not appear to permeate the membrane to any significant extent. Monosaccharide pentoses and hexoses are preferred in concentrations of from about 7.0 to 37.5%, preferably about 15% weight by volume. Xylose, glucose, ribose, mannose and fructose are employed to particular advantage.

The use of a water soluble, biologically compatible polymer, or a mixture of polymers at least one type of which is amphipathic, in addition to the carbohydrate, adds significantly to the recovery of cells retaining their light scattering and staining characteristics. The polymers will preferably be amphipathic, meaning that there are hydrophilic and hydrophobic portions on a single molecule of the polymer. The mixture of polymers may be present in the buffered freezing solution in total concentrations of from 0.7% (by weight) up to saturation. Preferably, each of the polymer types in the mixture has a molecular weight in the range of from about 1K to about 600K (number average molecular weight). Preferably, at least one of the types of polymers of the mixture will preferably have a molecular weight from about 5K to 400K, and most preferably from 20K to 360K. Also, one of the types of polymers of the mixture will preferably have a molecular weight in the range of about 100K to about 600K, most preferably in the range of about 100–500K. For a mixture of two different polymer types, each of the polymer types may be present in a concentration of from about 0.35% (by weight) up to its limit of solubility in the buffered freezing solution. Polymers selected from the group consisting of polyvinylpyrrolidone (PVP), polyvinylpyrrolidone derivatives, dextran, dextran derivatives, amino acid based polymers (i.e., proteins) and hydroxyethyl starch (HES) may be employed. Other amphipathic polymers may be used, such as poloxamers in any of their various forms. In a preferred embodiment for lymphocytes, a single polymer species, PVP, is employed in the buffered lyophilization solution. In a preferred embodiment for red blood cells, a mixture of PVP (molecular weight in the range of about 20K–360K) and HES (molecular weight in the range of about 100K–500K) is employed in the buffered freezing solution.

In addition, the freezing buffer may contain a cell-stabilizing agent which prolongs the period during which the cells, after reconstitution, maintain their desirable light scatter properties. Such agents include cupric chloride, ATP and interleukin-2. These freezing buffers are also be utilized to freeze cells or cell-like materials, without sublimation. Upon thawing, the cells or cell-like materials will be suitable as standards for live cells in cytometry.

As is shown by the embodiments set forth below, the described solutions provide media which permit cells, particularly lymphocytes, to be subjected to the stresses of freezing, water sublimation and reconstitution and to form freeze-dried cells which may be reconstituted to yield cells which have normal light scattering and retain surface antigens determinable by staining and flow cytometry.

The present invention is applicable to provide frozen storage of viable cells for use as reagents in diagnostic tests or as instrument calibration standards. In this application the same cryopreservative media used to protect cells to the freezing step in lyophilization can be used to maintain frozen stocks of reagent cells, which upon thawing can be used directly or optionally washed free of cryopreservatives.

Unless indicated otherwise by the terminology or the context, all percentages set forth herein are expressed as weight percentages (i.e., weight of the solute versus the total weight of the solution).

The term lyophilization is broadly defined as freezing a substance and then reducing the concentration of one of the solvents, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells, cell membranes or cell "ghosts" to withstand long-term storage at room temperature or under refrigeration. In the method described herein, cells may be lyophilized to a residual water content of less than 10%, preferably less than 5%, and most preferably to a water content of less than 3%.

Alternatively, in lieu of lyophilization, the attached cells or cell-like materials may be evaporatively dried. While the cells or cell-like materials may thus have a higher residual moisture content than that produced by lyophilization, this process requires no freeze-drying equipment, although some of the storage advantages of lyophilized products may be reduced.

The buffered freezing solution may contain, in addition to the monosaccharide and amphipathic polymer mixture, adjuvants, buffering agents, salts, cofactors, and the like. A particularly preferred freezing buffer contains the following components:

BUFFER 1

| | |
|---|---|
| 10.0 mM Glutathione (reduced) | 3.07 g/l |
| 10.0 mM Inosine | 2.68 g/l |
| 5.0 mM Adenine | 0.69 g/l |
| 0.75 mM Nicotinic acid | 0.09 g/l |
| 0.75 mM Glutamine | 0.11 g/l |
| 0.49 mM $MgCl_2.6H_2O$ | 0.10 g/l |
| 1.47 mM $KH_2PO_4$ | 0.20 g/l |
| 8.1 mM $Na_2HPO_4.7H_2O$ | 2.17 g/l |
| 1.7 M Dextrose | 306.3 g/l |
| 3.0 wt. % PVP (m.w. 360,000); | 30 g/l |
| 15.0 wt. % M-HES (m.w. 500,000): | 150 g/l |

Other preferred freezing buffers are

BUFFER 2

15% w/v PVP (40,000 MW)

13.5 w/v glucose 8.1 mM sodium phosphate 1.47 mM potassium phosphate 0.89 mM magnesium chloride pH 7.2 and

BUFFER 3

15% w/v PVP (40,000 MW)

13.5% w/v glucose 100 mM (tris-hydroxymethylaminomethane)

0.89 mM magnesium chloride pH 7.4

In a typical lyophilization procedure used to practice the present invention, cells to be lyophilized are washed, preferably on a cell washer (such as the COBE 2991) with dextrose saline.

The cells are mixed in a freezing container with freezing buffer. If red cells are used, a typically useful hematocrit is 30%.

The freezing buffer is preferably as described above, with the advantages of using a polymer mixture as shown by experimentation, the results of which are set forth in Table 1. As a control, one run was performed using only 20% 24K PVP as the polymer.

The freezing container is placed on the cooled shelf of a conventional shelf freeze-dryer, and the shelf temperature is lowered to freeze the cell mixture. Once frozen, a vacuum is applied and the samples are allowed to dry until the sample is thoroughly dried.

To reconstitute the dried samples, an equal volume of reconstitution buffer prewarmed to 37° C. is added to samples and agitated until sample is fully hydrated. The reconstitution buffer may contain a polymer as described above in connection with the freezing buffer (concentration preferably in the range of about 1–20 wt. %) which is amphipathic having a MW in the range of 1–600K, preferably 1–360K. A polymer containing reconstitution buffer is preferred for lyophilized red blood cells.

The preferred method of reconstitution for lyophilized lymphocytes is to soak the lyophilized cells in salt solution, preferably sodium chloride solution, for a period of from 5 to about 120 minutes at room temperature. Typical concentration of the reconstitution solutions is from 0.1 to 1.0 M sodium chloride, with 0.3 M sodium chloride being preferred.

A preferred reconstitution buffer to optimize recovery of cells such as erythrocytes is as follows:

| | |
|---|---|
| 5.0 mM ATP | 2.76 g/l |
| 1.47 mM $KH_2PO_4$ | 0.20 g/l |
| 8.1 mM $Na_2HPO_4.7H_2O$ | 2.17 g/l |
| 19.0% 10K PVP | 190.0 g/l |

For reconstitution of intact cells into a liquid suspension the reconstituted sample is prediluted with an equal volume of reconstitution buffer and agitated until thoroughly mixed. The reconstituted and prediluted cells are centrifuged at room temperature.

The cell pellet is resuspended in wash buffer and centrifuged. The wash buffer will preferably contain a polymer as described above in connection with the lyophilization buffer (concentration preferably in the range of about 1–20 wt. %) which is amphipathic having a MW in the range of 1–600K, preferably 1–360K.

The preferred wash buffer, again to optimize recovery of intact cells in liquid suspension, is as follows:

| | |
|---|---|
| 10.0 mM Inosine | 2.68 g/l |
| 5.0 mM Adenine | 0.69 g/l |
| 0.75 mM Nicotinic acid | 0.09 g/l |
| 0.75 mM Glutamine | 0.11 g/l |
| 0.49 mM $MgCl_26H_2O$ | 0.10 g/l |
| 30.0 mM KCl | 2.24 g/l |
| 30.0 mM NaCl | 1.75 g/l |
| 10.0 mM $Na_2HPO_4.7H_2O$ | 2.68 g/l |
| 20.0 mM Glucose | 3.60 g/l |
| 16.0% 40K PVP | 160.0 g/l |

The cell pellet can optionally be resuspended in a diluent buffer at a 10–50 fold dilution and centrifuged.

The preferred diluent buffer is as follows:

| | |
|---|---|
| 129.5 mm NaCl | 7.57 g/l |
| 5.0 mm $Na_2HPO_4.7H_2O$ | 1.34 g/l |

Assays based on recovered intact red cells can take advantage of the red pigment (hemoglobin) in the cells as a convenient tracer. To determine the hemoglobin recovery in reconstituted intact red cells a 200 uL sample is centrifuged for 5 min. at 5000 rpm. The cell pellet and supernatant are separated and 180 uL of water is added to the pellets, which are lysed by vortexing. To each sample 1 mL of Drabkins reagent is added, and after standing at R.T for 15 min. the absorbance at 540 nm is determined. Recovery=$A_{540}$ pellet/$A_{540}$ pellet+$A_{540}$ supernatant.

To determine whole blood stability of reconstituted red cells at 37° C. $^{51}$Cr as sodium chromate in a 1 mCi/ml sterile NaCl solution is added to a sample of reconstituted cells. In this standard assay $^{1}$Cr binds to cell hemoglobin inside the cells. Five μCi of $^{51}$Cr is added for every 0.1 ml of packed RBC pellet. The labelled pellet is incubated 15 min. at 37° C. after which the labelling reaction is stopped by addition of 1 ul of ascorbic acid (50 mg/ml in buffer) to every 0.1 ml of pellet. The pellet is then allowed to incubate another 5 min. at room temperature. The labelled sample is then washed 2 to 3 times in transfusion buffer. An aliquot of labelled cells is then transferred to 5 ml of autologous whole blood and the stability determined by the lysis of labelled cells at time points up to 24 hours. The amount of free $^{51}$Cr in the supernatant after centrifuging indicates the amount of cell lysis. For convenience, a 4-hour incubation is used, since lysis (if any) is complete by then.

Cell stability data (using the $^{51}$Cr tracer) show the stability and integrity of the lyophilized, reconstituted red blood cells. The $^{51}$Cr binds to the internal cell hemoglobin, and is released into the assay supernatant (therefore, lost) if the cells lyse. Thus, retention of $^{51}$Cr in the pellet measures cell integrity.

The present invention also provides methods for the manufacture of lyophilized or dry control cell standards of known antigen type, which can be used to either calibrate or quality control automated instruments or human operators.

In particular, the present invention is particularly useful to freeze or lyophilize white blood cells for storage which, when reconstituted, exhibit light scatter and surface antigen staining characteristics comparable to whole blood lysates. White blood cells may be isolated as fractions from whole blood. Other cell types, such as monocytes and granulocytes also survive lyophilization according to the invention and retain differential light scatter properties. Hence, the present invention provides a method for producing storable white blood cells which are suitable, when reconstituted, for flow cytometry calibration and quality control.

The present invention is applicable to antibody-coated cells, including mammalian and human cells. The cells may be precoated by known methods prior to freezing or lyophilization, or alternatively coated after reconstitution. Preferably the antibody-coated cells may be coated with fluorescently tagged antibodies where the antibodies are derived from polyclonal sera or monoclonal antibodies derived from hybridoma cultures. These fluorescently tagged antibodies which comprise the coatings on the cells may be utilized as calibration standards for cell sorting, cell counting, or analytical cytometry, such as flow cytometry or other types of analytical cytometry methods. The fluorescently tagged antibodies can also be added after the lyophilized cells have been reconstituted, for example, by adding anti-CD4 and anti-CD8 antibodies to reconstituted lymphocytes.

In addition to red blood cells, the present invention may be used, for example, for tissue typing using other types of cells such as lymphocytes which carry HLA (Human Leukocyte Antigens) antigens. Artificial cell systems that include a lipid membrane such as liposomes and hemosomes which comprise antigen-carrying lipid vesicles may be utilized.

The present invention is particularly useful for preparation of frozen or lyophilized whole blood to preserve blood of donors having unusual blood characteristics, particularly in white blood cells. Typically, the fresh blood from such donors is treated with a lysing agent to lyse the erythrocytes, and the lysed mixture containing the cell stroma, hemoglobin and other erythrocyte intracellular matter is directly analyzed in a flow cytometer, using software that electronically differentiates the red cell debris from the platelets, lymphocytes and other white cells. The lymphocytes, leukocytes, monocytes, etc. are used as standards for their unusual characteristics. In accordance with the present invention, whole blood from donors may be preserved in a frozen or lyophilized state and retain their characteristics suitable to serve as standards instead of fresh cells or freshly collected whole blood.

Furthermore, the present invention may be utilized on cellular membranes, particularly purified cellular membranes. The membranes may be any type of cell membranes but in particular mammalian or human cell membranes. Such membranes may be prepared by conventional methods from erythrocytes, lymphocytes, platelets, peripheral blood cells, stem cells and the like. A simple method involves hypotonic lysis of intact cells, which yields residual empty cell stroma comprised of all membrane, cytoskeleton, end integral and peripheral membrane associated proteins.

EXAMPLE 1

Lymphocytes were prepared from whole blood according to the protocol described for use of the HISTOPAQUE® 1077 (Sigma Diagnostics) solution for recovering mononuclear cells. The lymphocytes were lyophilized using lyophilization Buffer 2 (3 ml) for 42 hours, then stored @4° C. for about 30 days. A two-step reconstitution protocol was used. First, 3.0 ml of 0.3M. NaCl was added and the cells allowed to rehydrate for 15 minutes at room temperature, then a 1.0 ml sample was immediately analyzed in a Coulter Epics Profile FCM. The lymphocytes scattered light comparably to controls, but granulocytes were shifted relative to fresh blood.

However, the light scatter plot shows that cells in the sample were intact, i.e., they survived the lyophilization and rehydration, and retain the differential light scattering property of fresh lymphocytes.

Forty-five minutes after the rehydration with NaCl solution, 2.0 ml of distilled water were added the remaining cell suspension (2.0 ml). Fluorescent antibody agents for CD4 and CD8 surface markers were added (FITC T4 and RDI T8, sold by Coulter), and the stained sample was analyzed by Coulter's Epics Profile Analyzer. Control samples (fresh anticoagulated whole blood) were run in parallel in commercial lysis solution to remove red blood cells. The ratio of staining shows a 1.9:1 CD4:CD8 ratio (normal is 1.5 to 2.5:1). This fluorescent antibody staining profile shows that the rehydrated cells retain the ability to be stained after lyophilization, 30 days refrigerated day storage and rehydration in 45 minutes at room temperature.

EXAMPLE 2

Lymphocytes were separated from whole blood using the protocol and the tube of the LeucoPREP™ cell separation device (Becton Dickinson & Co.), then lyophilized in 250 ml. lyophilization Buffer 2 containing 0.9 mM cupric chloride, for 23 hours. The sample was reconstituted for 15 minutes in 500 microliters of 0.3M NaCl/3 mMATP/0.1% BSA/100 microliter/ml interleukin 2. After 15 minutes 100 microliters of samples were transferred into 200 microliters of the same rehydration buffer. Samples (non-stained) were analyzed in a Coulter Epics Profile Analyzer for scattering, with fresh whole blood as a control. The lymphocytes in the light scatter plot appeared precisely in the bitmap defined by the fresh blood standard.

EXAMPLE 3

Lymphocytes were separated from whole blood by the protocol in Example 2, then lyophilized either in (a) Buffer 2, modified to contain 9 mM cupric chloride/3mMATP/0.1% BSA/100 U/ml interleukin-2; or (b) Buffer 3, modified to contain 0.9 mM cupric chloride. Samples were reconstituted for 15 minutes either in 500 microliters of 0.3 M NaCl, with or without ATP-BSA-IL2. Samples lyophilized with ATP-BSA-IL2 were reconstituted in 0.3 mMNaCl. Then 168 microliters of sample were transferred to a tube containing 336 microliters of 0.3M NaCl/3 mMATP/0.1% BSA/100 microlit./ml IL-2. Samples were analyzed by Becton-Dickinson FACS 4 with Cyclops software for light scattering patterns.

In the light scatter plots for cells lyophilized in modified Buffer 2, the lymphocytes and granulocytes scatter closer to the corresponding position for fresh whole blood standard than do the nonlyophilized lymphocytes and granulocytes separated from whole blood by the HISTPAQUE® protocol. Also, the stability of the rehydrated cells (derived from light profile changes over time) is improved, in the presence of copper ion, ATP, BSA and IL-2.

In the light scatter plots of the lymphocytes lyophilized in modified in Buffer 3, some lymphocytes scatter higher on the x-axis (forward scattering) than in the standard.

EXAMPLE 4

Lymphocytes are separated from peripheral whole blood by the Ficoll-Hypaque protocol in Example 1, then washed three times in culture medium (RPMI). The cells are counted using a hemacytometer, and a sufficient volume of the cell suspension is transferred to a centrifuge tube. The cells are pelleted and the surplus medium removed. The cell pellet is gently mixed with (a) Buffer 2, modified to contain 9 mM cupric chloride/3mMATP/0.1% BSA/100 U/ml interleukin-2; or (b) Buffer 3, modified to contain 9 mM cupric chloride. The final cell concentration is adjusted to $5 \times 10^6$ cells/ml. The cells are then frozen and stored in a $-20°$ C. freezer. Samples are thawed at 37° C. and are then either analyzed for cell viability or diluted directly into commercial flow cytometry diluent and analyzed by using a Becton-Dickinson FACS 4 for light scattering patterns.

Alternatively, anticoagulated whole blood is concentrated by a gentle centrifugal spin, and as much residual plasma removed as possible. About 1.0 ml whole blood concentrate is mixed with 1.0 ml of either cryopreservative solution described above, by dropwise addition of the cryopreservative solution. The blood sample is then frozen and stored in a $-20°$ C. freezer. The thawed samples are then either analyzed for cell viability or subjected to flow cytometry analysis as before.

For the cell viability assay, 100 microliters of thawed cell suspension (either lymphocytes or whole blood) is diluted 1:10 with phosphate-buffered saline (PBS), then 100 microliters of the diluted cells are mixed with an equal volume of an acridine orange/ethidium bromide working solution. (The dye solution is prepared as a stock solution containing 1 milligram acridine orange and 1 milligram ethidium bromide in 1 ml ethanol, then the stock solution is diluted 1:100 in PBS to yield a fresh working solution). The stained cells are then examined under a fluorescence microscope. Viable cells appear dull orange while non-viable cells appear green.

In Table X we show the cell viability data for frozen-thawed lymphocytes and whole blood prepared by freezing in modified Buffer 2, followed by storage at $-20°$ C., thawing at 37° C. and staining with acridine/ethidium dye. Recovery of cells that appear to retain an intact morphology by microscopic examination is determined by comparing the cell concentration in the final sample versus the starting concentration of $5 \times 10^6$ cells/ml in all samples. Viable cell recovery represents the percentage of recovered intact cells that stain viable using the fluorescent dye assay.

TABLE X

| Sample | Concentration of Intact Cells | Percent Intact Cell Recovery | Percent Viable Cell Recovery |
| --- | --- | --- | --- |
| Lymphocytes | $4.7 \times 10^6$/ml | 94 | 95 |
| Whole blood | $4.2 \times 10^6$/ml | 84 | 80 |

The large portion of recovered intact and viable cells suggests that the lymphocytes are essentially recovered intact from the ficoll-hypaque preparations, and thus would exhibit normal scatter plots in a flow cytometry test. The whole blood sample also appears reasonably intact after thawing, and therefore indicates that in a commercial application (in which a lysis solution would be used to eliminate the red cells), the white blood cells in that sample would provide light scatter plots acceptable as a cytometry standard.

EXAMPLE 5

Liquid phase tests on red blood cells

Test 1

Red cell samples were lyophilized using one polymer or a polymer mixture, and the whole blood stability of $^{51}$Cr labeled reconstituted cells was studied.

The results are described as follows in Table 1.

TABLE 1

| Lyophilization Buffer Polymer Composition | Hemoglobin Recovery | Mean Cellular Volume | 4 hr. Whole Blood Stability |
| --- | --- | --- | --- |
| 10% 24K PVP (Control) | 24.3 ± 2.2 | 87.6 ± 6.2 fl | 50.5 ± 15.5% |
| 5% 24K PVP 15% 500K HES | 27.3 ± 2.0% | 74.7 ± 11.3 fl | 73.7 ± 9.6% |
| 10% 24K PVP 10% 500K HES | 28.1 ± 2.7% | 84.3 ± 8.1 fl | 67.8 ± 9.5% |
| 10% 24K PVP 5% 500K HES | 23.2% | 67.0 fl | 78.7% |

It can be seen that by using a mixture of polymers the 4-hr. whole blood stability is significantly improved versus the control sample using one polymer.

Test 2

In an alternative test, packed red blood cells are mixed in a container with lyophilization buffer at a hematocrit of 30%. The lyophilization buffer is described below for Table 2.

The container is then placed in a standard shelf lyophilizer (Virtis SRC-15 Lyophilizer) and frozen. The frozen sample is then placed under a vacuum. The sample is allowed to dry, with a total weight loss of 58±2%. The sample is returned to room temperature and the vacuum is removed.

To reconstitute the dried samples, an equal volume of pre-warmed reconstitution buffer is added to samples and agitated until sample is fully hydrated.

The reconstitution buffer is as previously described.

The reconstituted sample is prediluted with an equal volume of reconstitution buffer and swirled until thoroughly mixed. The reconstituted and prediluted cells are transferred to a COBE 2991 Blood Cell Washer, centrifuged, and repeated until all of the reconstitution buffer volume is added to the Cobe bag. The cells are washed by the automatic protocol of the Cell Washer with the following solutions:

1. Wash buffer: 500 ml.
2. Pellets washed with Diluent buffer: 500 ml.
3. Transfusion buffer: 500 ml.

All samples are 30% hematocrit in Table 2. The lyophilization buffer used to prepare the samples in Table 2 contained a mixture of 3% 360K PVP and 15% 500K HES.

TABLE 2

| Sample No. | % Hb Recovery | MCV | % Whole Blood Stability |
|---|---|---|---|
| 1 | 27.3 | 80.0 | 73.3 |
| 2 | 26.2 | 76.1 | 73.3 |
| 3 | 29.6 | 78.7 | 62.5 |
| 4 | 27.2 | 80.5 | 70.9 |
| 5 | 29.4 | 76.1 | 70.6 |
| 6 | 24.7 | 76.1 | 71.7 |
| 7 | 26.5 | 80.0 | 68.2 |
| MEAN | 27.3 ± 1.77 | 78.2 ± 2.0 µm$^3$ | 70.1 ± 3.8 |

Note:
MCV = mean cell volume

Test 3

A test was repeated with the substitution of 200K HES for 500K HES in a given HES/PVP polymer mixture in the lyophilization buffer. The results are described in Table 3.

TABLE 3

| Lyophilization Buffer Polymer Composition | Hemoglobin Recovery | Mean Cellular Volume | 4 hr. Whole Blood Stability |
|---|---|---|---|
| 5% 24K PVP 10% 200K HES | 14.7% | 77.3 fl | 65.1% |
| 10% 24K PVP 10% 200K HES | 27.7 ± 4.4% | 81.8 ± 1.8 fl | 61.6% |

The whole blood stability is reduced if the cells are lyophilized using the 200K HES, compared to using 500K HES as in Table 2.

Test 4

In a test for 40% hematocrit mixtures with washed red blood cells, the polymer composition used in these lyophilization buffers, was 5:15% 24K PVP:500K HES. The glucose concentration in the 40% lyophilization buffers is increased to 2.3 M (441.37 g/l). The results are described as follows in Table 4:

TABLE 4

| Sample Hct. | Lyophilization Buffer Polymer Composition | Hemoglobin Recovery | Mean Cellular Volume | 4 hr. Whole Blood Stability |
|---|---|---|---|---|
| 40% | 20% 24K PVP (Control) | 28.2 ± 3.5% | 80.0 ± 7.9 fl | 39.5 ± 1.0% |
| 40% | 5% 24K PVP 15% 500K HES | 29.2 ± 3.0% | 82.9 ± 12.9 fl | 70.1 ± 14.8% |

The 4-hr. whole blood stability was significantly increased using a polymer mixture as compared to using a single polymer.

Test 5

Using 360K PVP instead of 24K PVP in a given HES/PVP polymer mixture in the lyophilization buffer, the test was repeated. The results are described in Table 5.

TABLE 5

| Lyophilization Buffer Polymer Composition | Hemoglobin Recovery | Mean Cellular Volume | 4 hr. Whole Blood Stability |
|---|---|---|---|
| 3% 360K PVP 15% 500K HES | 24 ± 6% | 79 ± 6 fl | 76 ± 10% |

The blood cells may be lyophilized to form dry beads, pellets or droplets, and packaged in compartmented blister packs or glass vials.

In another embodiment, blood cells coated with antibodies can be lyophilized and reconstituted for use as markers various assays. The lyophilized antibody-coated red blood cells can be packed in microliter plates or blister packs for this application.

In another embodiment, the lyophilization medium or any of the reconstitution or wash solutions may be adjusted so that the reconstituted cells or cell-like materials are incubated with antibodies (either antisera or plasma or serum from blood) in an incubation medium that optimizes a desired antibody-antigen reaction. For example, certain reactions are enhanced at lower pH or ionic strength, or by a polymer such as PEG (polyethlyeneglycol). The enhancer may be a polymer, such as PEG, a protein, such as BSA, or other macromolecular species.

What is claimed is:

1. An analytical method of examining cells or cell-like materials wherein characteristics of said cells or cell-like materials are compared to corresponding characteristics of a flow cytometry standard, the improvement comprising the step of examining said standard wherein said standard comprises reconstituted lyophilized cells or cell-like materials in which the membrane properties, light scatter properties and cell-surface antigens are preserved, said reconstituted lyophilized cells or cell-like materials being lyophilized by the steps of:

(a) immersing the cells or cell-like materials in a cryoprotective medium comprising a monosaccharide and a water-soluble amphipathic polymer having a number average molecular weight range of about 1K to about 600K; and (b) lyophilizing said cells or cell-like materials and cryoprotective medium.

2. An analytical method of examining cells or cell-like materials wherein characteristics of said cells or cell-like materials are compared to corresponding characteristics of a flow cytometry standard, the improvement comprising the step of examining said standard wherein said standard comprises cells or cell-like materials recovered from a frozen state in which the membrane properties, light scatter properties and cell-surface antigens are preserved, said cells or cell-like materials recovered from a frozen state being frozen by the steps of:

(a) immersing cells or cell-like materials in a cryoprotective medium comprising a monosacchadde and a water-soluble amphipathic polymer having a number average molecular weight range of about 1K to about 600K; and (b) freezing said cells or cell-like materials and cryoprotective medium.

3. A method according to claim 1 or 2 wherein said analytical method comprises cytometric examination of said cells or cell-like materials.

4. A method according to claim 1 or 2 wherein said cells or cell-like materials comprise at least one member selected from the group consisting of peripheral blood cells, whole blood, liposomes and hemosomes.

5. A method according to claim 4 wherein said cells or cell-like materials comprise peripheral white blood cells.

6. A method according to claim 5 wherein said peripheral white blood cells consist essentially of lymphocytes, monocytes and granulocytes.

7. A method according to claim 4 wherein said cells or cell-like materials comprise whole blood.

8. A method according to claim 4 wherein said cells or cell-like materials are bound to antibodies.

9. A method according to claim 8 wherein said antibodies are fluorescently-labelled.

10. A method according to claim 6 wherein said peripheral white blood cells exhibit preservation of CD4 and CD8 lymphocyte antigens.

11. A method according to claim 6 wherein said peripheral white blood cells exhibit preservation of optical properties.

12. A method according to claim 11 wherein said optical properties comprise light scatter, light reflection, light transmission and optical density.

13. An analytical method of examining cells or cell-like materials wherein characteristics of said cells or cell-like materials are compared to corresponding characteristics of a standard, the improvement comprising the step of examining said standard wherein said standard comprises cells or cell-like materials recovered from a frozen state, said cells or cell-like materials recovered from a frozen state being frozen by the steps of:

(a) immersing cells or cell-like materials in a cryoprotective medium comprising a monosaccharide and a water-soluble amphipathic polymer having a number average molecular weight range of about 1K to about 600K; and (b) freezing said cells or cell-like materials and cryoprotective medium for more than an hour.

* * * * *